US008530433B2

(12) United States Patent
Xin et al.

(10) Patent No.: US 8,530,433 B2
(45) Date of Patent: Sep. 10, 2013

(54) USE OF ICARISIDE II IN MANUFACTURE OF PRODUCTS FOR PREVENTING OR TREATING MALE OR FEMALE SEXUAL DYSFUNCTION

(75) Inventors: Zhongcheng Xin, Beijing (CN); Hua Xin, Beijing (CN); Zhenji Tian, Beijing (CN)

(73) Assignee: Bjo-Biomed Ltd, Beijing (CN)

( * ) Notice: Subject to any disclaimer, the term of this patent is extended or adjusted under 35 U.S.C. 154(b) by 162 days.

(21) Appl. No.: 12/997,423

(22) PCT Filed: Jun. 12, 2009

(86) PCT No.: PCT/CN2009/000650
§ 371 (c)(1),
(2), (4) Date: Jan. 28, 2011

(87) PCT Pub. No.: WO2009/149621
PCT Pub. Date: Dec. 17, 2009

(65) Prior Publication Data
US 2011/0301106 A1    Dec. 8, 2011

(30) Foreign Application Priority Data
Jun. 13, 2008   (CN) .......................... 2008 1 0110687

(51) Int. Cl.
*A61K 31/70*        (2006.01)

(52) U.S. Cl.
USPC .................................. 514/27; 514/25; 514/33

(58) Field of Classification Search
USPC ................................................ 514/25, 27, 33
See application file for complete search history.

(56) References Cited

U.S. PATENT DOCUMENTS 6,399,579 B1 *   6/2002   Lenoble et al. ................. 514/25
6,916,845 B2 *   7/2005   Xin ............................... 514/456

FOREIGN PATENT DOCUMENTS

CN   1199647 C       5/2005
WO   2007064085 A1   6/2007

OTHER PUBLICATIONS

Zhao Yanhong et al., "Studies on Rat Intestinal Absorption of the Total Flavones of Epimedium in Situ", Feb. 2008, vol. 43, No. 3, p. 191.

* cited by examiner

*Primary Examiner* — Elli Peselev
(74) *Attorney, Agent, or Firm* — The Webb Law Firm

(57) ABSTRACT

The present invention provides the use of icariside II or extract comprising thereof in manufacture of products for preventing or treating male or female sexual dysfunction, in particular, the use for improving pathological or organical changes in erectile tissues of patients with erectile dysfunction.

11 Claims, 4 Drawing Sheets control    icariside II    icariside II    icariside II
           (10nm)       (100nm)     (1000nm)

USE OF ICARISIDE II IN MANUFACTURE OF PRODUCTS FOR PREVENTING OR TREATING MALE OR FEMALE SEXUAL DYSFUNCTION

FIELD OF THE PRESENT INVENTION

The present invention relates to use of icariside II or extract comprising icariside II in manufacture of products for the preventing or treating sexual dysfunction in male and female, especially for improving organical pathological changes on erectile tissues of patients with erectile dysfunction.

BACKGROUND OF INVENTION

Icariside II is a known compound; its structure is as follows:

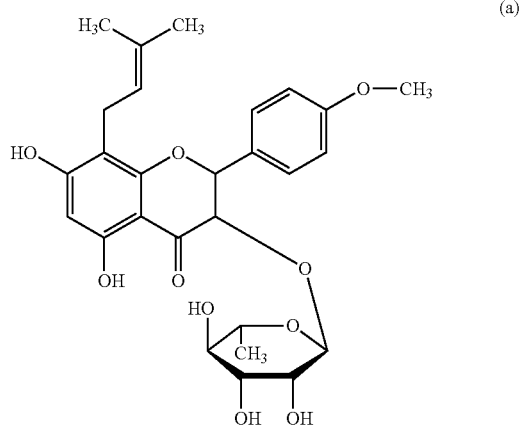

(a)

It is reported that icariside II has a skin whitening effect (WO2008/035918).

The male sexual function is consisted by a series of events, including the penile erection with blood hemodynamic changes taking place in the erectile tissue of corpus cavernosum under the regulation of nervous system during sexual stimulation. Firstly, with sexual stimulation or sexual desire, the function of corpus cavernosum was controlled by the efferent nerve from the pelvic nerve, under the central regulation of erectile regulation center in brain and spinal cord. The parasympathetic nerve ending of the efferent nerve releases acetylcholine, which activates endothelial nitric oxide synthase (eNOS) in endothelial cells to promote nitric oxide (NO) generation, meanwhile, nNOS from non-adrenanic non-cholinergic (NANC) nerve promote NO generation. NO activates soluble guanylate cyclase (sGC) in the smooth muscle cells to promote cGMP synthesis. cGMP activating protein G (PKG) and the intracellular calcium is decreased to induce smooth muscle relaxation. Then penis cavernosal artery dilation and cavernous sinus expanding are induced for increasing the arterial blood perfusion in the corpus cavernosum and the vein under the albuginea is pressed by expanded corpus cavernosm, thereby blocking the venous outflow from corpus cavernosm induce penile erection. cGMP could be regulated by cGMP specific phosphodiesterase type V (PDE5) to lose activity. The increase of sympathetic nerve activity leads to contraction of smooth muscle, which turns to flaccid status. Therefore, erectile response depends on the integrity of neural structure and function, corpus cavernosum smooth muscle, endothelial cell structure, and regulated by NO-cGMP signaling pathway.

With the advance of modern science and technology, it had been identified that more than 50% of sexual dysfunction patients suffered from spinal cord and brain peripheral nerve injury, hypertension, atherosclerosis, and diabetes etc. In addition, these diseases caused penile corpus cavernosum nerve injury, and dysfunction of smooth muscle and endothelial cells of penile corpus cavernosum. Studies show that organic erectile dysfunction caused by diabetes, hypertension, atherosclerosis, nerve damage and other diseases is related to the pathological changes on penile corpus cavernous nerve, corpus cavernosum smooth muscle and endothelial cell, while the molecular biology study showed a significantly lower levels of NOS activity or gene expression in corpus cavernosum is closely related to those conditions.

Although the oral agent phosphodiesterase (PDE5) inhibitor, such as sildenafil, showed a reliable one time effects for treating erectile dysfunction on demanded, if it is taken before sexual activity, but it showed no effects in more than 20% of patients with severe organic erectile dysfunction. In addition, PDE5i showed no therapeutic effect on the pathological changes to the erectile tissue of penis. Meanwhile, it caused varying degrees of side effects such as flushing, headache, visual disturbances, low blood pressure and back pain, etc. More importantly, it has potentially risk in patients with cardiovascular disease and is strictly inhibited from co-administration with nitrite. Actually, intracavernous injection of vascular relaxation drugs such as paparvarin, phentolamine or prostaglandin E1 etc is also used for treating erectile dysfunction. However, this therapy had no effect on more than 20% of patients with severe organic erectile dysfunction, and also showed no therapeutic effect on the pathophysiological changes to the penis of erectile dysfunction. Meanwhile, it caused side effects such as lower the blood pressure, headache and dizziness, local pain, persistent penile erection, penile fibrosis. The clinical application of intracavernous injection therapy is often prohibited.

Therefore, a new medication with a potential for preventing and treating erectile dysfunction and with therapeutic effects on pathological change to penile corpus cavernosm, such as promoting nerve regeneration, regulating the function of corpus cavernosum smooth muscle and endothelial cell and regulating NOS activity or gene expression, is highly desired clinically. However, there is no such a prevention and treatment drug by now.

Epimedium herb is used in traditional medicine and often served as the prescription strong tonic ingredient, but the mechanisms have not been clarified. Recent studies have shown that Epimedium contains many active ingredients, such as icariin, icariside I, icariside II, volatile oil, wax alcohol, alkanes, phytosterols, tannins, linoleic acid and so on. Also, some traces of magnoflorin, epimedoside A, epimedin A, B, C, querecetin, and anhydroicariin-3-O-rhamnoside were isolated recently. Icariside II is currently used as standard chemical reagent in laboratory. Previous study found that icariside II could selectively inhibit PDE5, but its PDE5 inhibiting potency is significantly lower than sildenafil when tested in vitro. The initial clinical trial in volunteers (with informed consent) with erectile dysfunction showed that a single oral administration of icariside II (500 mg/time) before sexual activity caused some improvement on erectile function, but the effect is not significant. These results indicated that icariside II have a weak potency in inhibiting PDE5 activity. A single oral administration of icariside II before sexual activity is not sufficient to treat erectile dysfunction as sildenafil.

SUMMARY OF THE INVENTION

The present inventors have unexpectedly found that icariside II significantly improvements patients with erectile dysfunction after orally taken 200 mg/day icariside II before sleep for four weeks. The pharmacological study shows that it not only has a slight inhibitory effect on PDE5, but also promotes nerve regeneration, and increases the smooth muscle content of corpus cavernosum and enhances the activity of NOS in endothelial cells as well as expression of nitric oxide synthase. These effects are related to EGFR signaling pathway. Therefore, icariside II has ameliorative or therapeutic effect on pathological changes in penis with erectile dysfunction.

The present invention thus relates to use of icariside II or extract comprising icariside II for the manufacture of a product for the prevention or treatment of sexual dysfunction in male and female.

The present invention also relates to a product for the prevention or treatment of sexual dysfunction in male and female, where said product comprises icariside II or extract comprising icariside II.

The present invention further relates to a method of prevention or treatment of sexual dysfunction in male and female, comprising administrating to a patient in need thereof a preventively or therapeutically effective amount of icariside II or extract comprising icariside II.

The present invention also relates to use of icariside II or extract comprising icariside II in manufacture of a product for improving pathological or organic tissues in patients with erectile dysfunction.

According to the invention, the term "product" refers to product for human, for example but not limited to health food or medicament.

According to the invention, the term "icariside II" refers to icariside II monomer or extracts or mixtures containing icariside II, wherein the extracts or mixtures containing no less than 50% (weight) of icariside II.

According to the invention, the term "carrier or excipient" refers to the excipients or carrier acceptable in foods or medicaments.

The present invention relates to a use of icariside II or extract comprising icariside II for the prevention or treatment of erectile dysfunction. Studies have shown that pathologic/organic erectile dysfunction account for 50% of patients with erectile dysfunction, which is caused by injury to the penis cavernous nerves, smooth muscle and endothelial cell, and it's pathological mechanism was related to significantly lower levels of nitric oxide synthase (NOS) activity and expression. Therefore, drugs that restore the function of nerve, smooth muscle and endothelial cell and restore NOS function and gene expression would have a role of preventing and treating of erectile dysfunction. The present inventors have unexpectedly found that icariside II and extract comprising icariside II promotes nerve regeneration, and increases the activity of smooth muscle of corpus cavernosum and enhances the activity of NOS in endothelial cells as well as expression of nitric oxide synthase. These effects are related to EGFR signaling pathway. Therefore, icariside II has ameliorative, preventive or therapeutic effect on pathophysiological changes in penis with erectile dysfunction.

According to the invention, icariside II and extract comprising icariside II can be used alone or in the form of a pharmaceutical composition. Pharmaceutical compositions comprise icariside II or extracts comprising icariside II as active ingredients and pharmaceutically acceptable carrier.

According to the invention, icariside II and extract comprising icariside II can be used alone or in the form of pharmaceutical compositions, for prevention and treatment of erectile dysfunction, nerve damage disease and endothelial cell dysfunction.

According to the invention, icariside II and extract comprising icariside II can be used alone or in the form of pharmaceutical composition. Pharmaceutical compositions comprise icariside II and extract comprising icariside II as active ingredients. The various dosage forms has a content of icariside II and extract comprising icariside II in the range from 5 mg to 500 mg.

The pharmaceutical compositions according to the invention may be prepared by means known in the art and administered orally, parenterally or locally. Oral formulations include, such as tablets, chewing, capsule, suspension, solution, etc; parenteral formulations include, such as injectable solutions; formulations for local administration include, such as creams, ointments, transdermal patches, sprays, and the like.

According to the invention, icariside II and extract comprising icarisidell are extracted by organic solvent or mixtures of organic solvent and water from Epimedium herb, or obtained from icariin by enzymatic digestion or biological synthetic methods. Organic solvents used include alcohols such as methanol, ethanol, halogenated alkanes such as dichloromethane, chloroform, ethers such as diethyl ether, ketones such as acetone, lipids such as methyl acetate, ethyl acetate, hydrocarbons such as hexane etc. Digestive enzymes, include hydrolase enzymes of various sugars or cellulose, such as $\alpha$ and $\beta$ glucosidases.

DETAILED DESCRIPTION OF THE INVENTION

The following Example is used to describe the invention in details, but does not mean that present invention is limited thereof.

Example 1

Preparation of Icariside II Extracts and Icariside II

Extraction Method (1)
Extracts Comprising Icariside II

Five hundred gram dried aerial part of Epimedium were ground and extracted with 10 L of 70% EtOH at 80 C.° for one hour, three times, three back, under reflux. Then the extract was filtered and the filtrate was concentrated. The ethanol extract was then suspended in 4 times water and allowed to sit for ahs to remove the chlorophyll and other waxes. Then after extraction with n-butanol for times, the extracts were combined and concentrated. Then the extracts were subjected to 40-60 mesh polyamide column and eluted with 30% ethanol. The elutes were concentrated and resolved in 70% ethanol (1:20) and kept still for 8 hours. After filtration, icariin was obtained. Then icariin was recrystallized with anhydrous ethanol (1:15) and extract comprising icariside II was obtained. HPLC analysis conformed that the content of icariside II is 50.2%.

Extraction Method (2)
Separation and Purification of Icariside II

Figure 1:
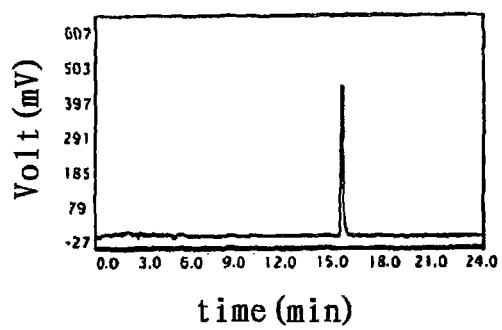
FIG. 1. HPLC detection of the purity of icariside II.

The extract comprising icariside II was dissolved in MeOH and adsorbed to silica gel to dry. Then it is loaded onto silica gel column (8×60 cm) and eluted with different ratio of $CHCl_3$ and MeOH (5:1, 4:1, 3:1, 2:1). The various fractions were concentrated and subjected to crystallization with $MeOH/H_2O$. A yellow crystal was obtained, which develops a color under UV and produces positive reaction in test with pauly reagent. HPLC analysis conformed that the content of icariside II is 99.8%. See FIG. 1.

Extraction Method (3)
Extraction and Detection of Extracts Comprising Icariside II Fifty grams icariin were added into sodium dihydrogen phosphate-disodium hydrogen phosphate buffer (pH5.5) and 100 ml β glucose. 100 ml of β glucosidase was added and the solution was heated to 40° C. with stirring for 24 hours in order to remove glucoside. Then stop heating and repeatedly extract with ethyl acetate. The ethyl acetate layer was pooled and dried. Then repeatedly extract with methanol. The HPLC analysis confirmed that the content of pure icariside II 50.1%. Thus extract comprising icariside II is obtained.

Extraction Method (4)
Separation, Purification and Detection of Icariside II

Extracts comprising icariside II were dissolved in methanol and repeatedly extracted and subject to concentrated crystallization for 5-8 times. Yellow crystal of pure icariside II was obtained. The crystal develops a color under UV and produces positive reaction in test with pauly reagent. HPLC analysis conformed that the content of icariside II is 99.8%.

Example 2

The Effect of Icariside II on Penile Nerve Regeneration in Old Rats

Materials and Methods

The 24-month-old Sprague-Dawley male rats were used. All experimental animals used in this study were under a protocol approved by the Institutional Animal Care and Use Committee. Rats were anesthetized by intraperitoneal injection of pentobarbital sodium (200 mg/kg). After midline incision on abdomen, major pelvic ganglion was carefully dissected from prostate. MPG culture and treatment: the Bilaterally MPG was rapidly removed and after washing with PBS, DCR were stripped from MPG and cut into 3 pieces with the same size.

Reduced Growth Factor Matrigel (RGFM) was diluted three times with serum free RPMI-1640 medium and placed in the 35 mm Petri dish on ice. The diluted RGFM were poured onto the cold sterilized glass cover slip and incubated at 37° C. for 1 hour in 35 mm Petri dishes to make the RGFM steady. Then each MPG was embedded in 40 μl of pre-cooled RGFM and maintained at 37° C. for 5 minute and cultured in RPMI 1640 with 1% penicillin-streptomycin that is maintained in humidified cell culture incubator containing 5% $CO_2$ at 37° C.

The cultured MPG tissues were randomly divided into 3 groups: control group, icariside II and sildenafil groups. The concentration of drug added into the medium were 0, 10, 100 and 1,000 nM, respectively. Three MGP from the younger groups and the three MPG from the older groups were cultured with designation dose for 48-72 hours.

Measurement of nerve axon growth: at the 48 and 72 hours, Nikon DXM1200 digital camera connected to Zeiss Axiovert microscope and ACT-1 software (20 times magnification) was used to observe the nerve axon growth on the MPG. The digital image was analyzed by Chemilmager 4000 and the length of the longest nerve axon was calculated.

Result

Figure 2:
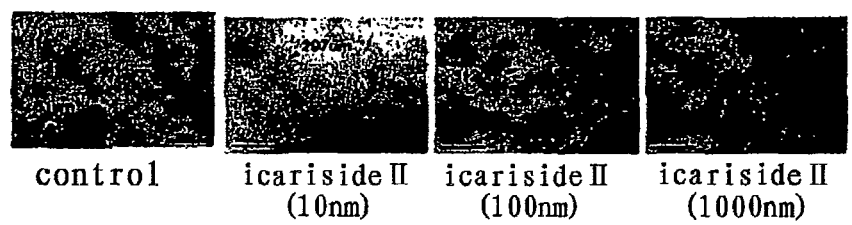
FIG. 2. Effect of icariside II and sildenafil in promoting regeneration of nerve axon in old rats.
Figure 3:
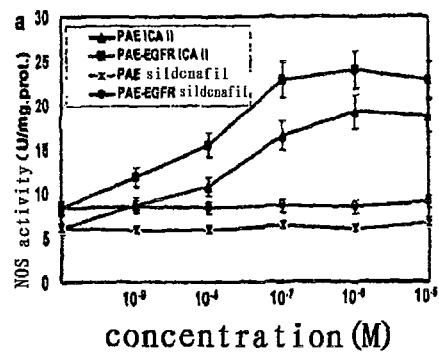
FIG. 3. Effect of icariside II and sildenafil on NOS enzyme activity in vascular endothelial cells (PAE).
Figure 4:
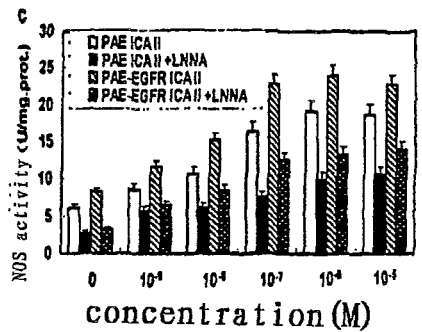
FIG. 4. Effect of nitric oxide synthase inhibitor (LNNA) and icariside II on NOS enzyme activity in vascular endothelial cells (PAE).
Figure 5:
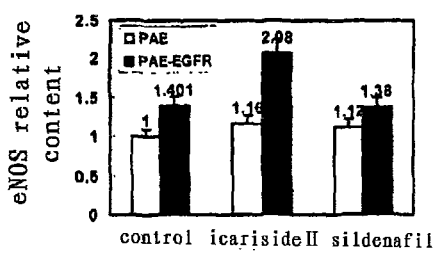
FIG. 5. Effect of icariside II and sildenafil on NOS activity in corpus cavernosum smooth muscle.
Figure 5:
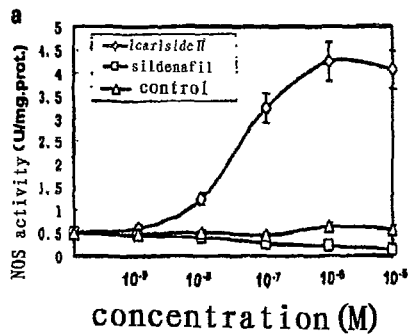
Figure 6:
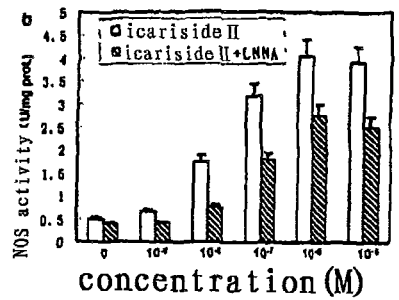
FIG. 6. Effect of nitric oxide synthase inhibitor (LNNA) and icariside II on NOS activity in corpus cavernosum smooth muscle cells.
Figure 7:
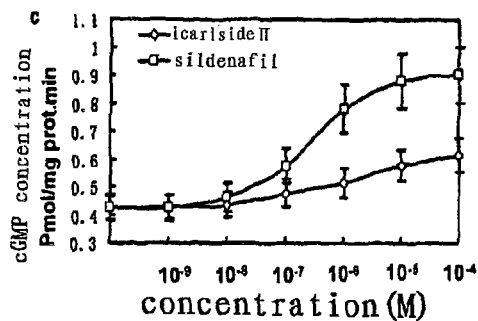
FIG. 7. Effect of icariside II and sildenafil on cGMP biosynthesis in corpus cavernosum smooth muscle cells.
Figure 8:
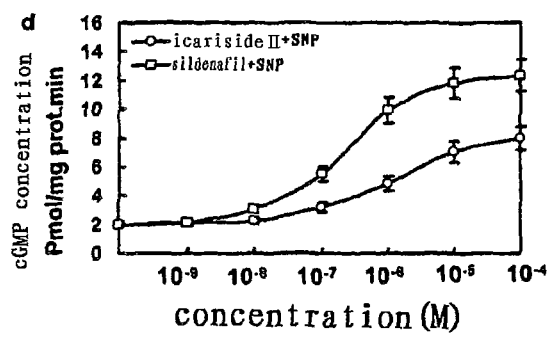
FIG. 8. Effect of icariside II and sildenafil on cGMP biosynthesis in corpus cavernosum smooth muscle cells upon stimulation with SNP.
Figure 9:
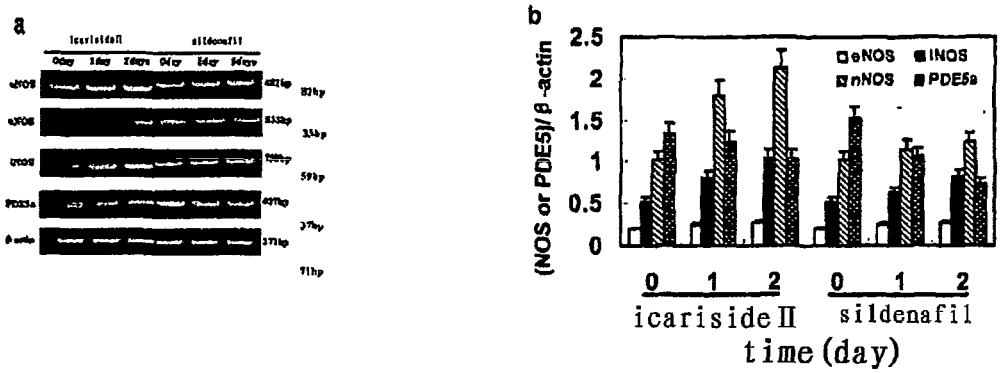
FIG. 9. Effect of icariside II and sildenafil on NOS isoforms and PDE5 mRNA expression.
Figure 10:
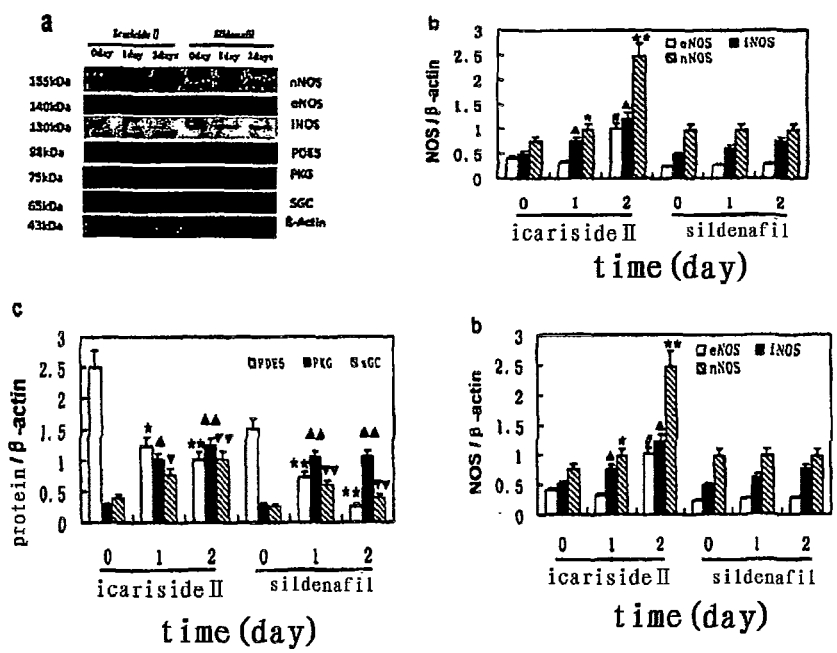
FIG. 10. Effect of icariside II and sildenafil on NOS isoforms, PDE5, PKG and sGC protein expression.

Different dose of icariside II (10 nM, 100 nM, 1000 nM) significantly promoted MPG axonal nerve dense growth in old rats (Table 1, FIG. 2). Treatment with icariside II (10 nM, 100 nM, 1000 nM) significantly increased MPG nerve axon growth ($p<0.01$) compared to control group, while different concentrations of sildenafil did not significantly affect the growth of MPG nerve axons ($p>0.05$). The results suggest that icariside II has a good role in promoting nerve regeneration and may prevent and treat erectile dysfunction in older men caused by diabetes, hypertension, atherosclerosis, nerve damage and other diseases.

TABLE 1

Effect of icariside II and sildenafil in promoting MPG nerve axon growth of old rats

|  | Control (n = 9) | Icariside II (n = 9) | Sildenafil (n = 9) |
| --- | --- | --- | --- |
| 10 nM | 122 ± 4.1 μm | 295 ± 5.3 μm* | 215 ± 2.6 μm |
| 100 nM | 111 ± 3.3 μm | 325 ± 4.1 μm* | 238 ± 3.5 μm |
| 1000 nM | 125 ± 4.2 μm | 406 ± 4.3 μm* | 219 ± 3.2 μm |

*P Value <0.01

Example 3

Effect of Icariside II on NOS Enzyme Activity in Vascular Endothelial Cells (PAE)

Method and Material

Porcine vascular endothelial cells (PAE) were provided by the Institute of Urology, Peking University. The determination of the effect of icariside II on NOS activity in the endothelial cell is conducted using NOS kit (Cayman Chemical company, Ann Arbor, Mich., USA). Vascular endothelial cells (PAE) were treated with different concentrations of icariside II (0, $10^{-9}$, $10^{-8}$, $10^{-7}$, $10^{-6}$, $10^{-5}$ and $10^{-4}$ M) (sildenafil as the control group). 180 μl lysate was added into each culture well. 20 μl supernatant was used for protein concentration assay with BCA protein kit. And, 100 μl supernatant was analyzed for NOS activity with NOS kit (Cayman Chemical company, Ann Arbor, Mich., USA). NOS activity (units/mg)=[(value$_{NOS\text{-}measure}$−value$_{NOS\text{-}blank}$)÷(38.3×$10^6$)]× [(2.15+supernatant volume)÷(15×supernatant volume)]÷ [protein concentration of each Petri dish].

Result

The activity of NOS enzyme was measured before and after treatment with icariside II (sildenafil as the control group) in order to determine the effect of icariside II on the function of endothelia cells. NOS enzyme activity in PAE endothelial cells was determined to as 6.03±0.54 u/mg at baseline. The NOS enzyme activity in the EGFR expressing PAE-EGFR was determined as 8.34±0.83 u/mg at baseline. When icariside II concentration is $10^{-8}$ M, the NOS activity is 10.71±1.09 u/mg. Icariside II significantly increased NOS II activity in PAE cells, (P<0.05). Treatment with $10^{-6}$ M of icariside II significantly increased NOS activity (19.1±1.891 u/mg) (P<0.01). In the EGFR expressing PAE-EGFR cells, $10^{-8}$ M icariside II increased NOS activity to 15.37±1.49 u/mg, which is 4.66 u/mg higher than the activity in PAE cells. Other concentrations of icariside II ($10^{-7}$, $10^{-6}$ and $10^{-5}$ M) also significantly increased NOS activity in PAE-EGFR cells compared to PAE cells (P<0.01). The results suggest that effect of icariside II on NOS enzyme activity may be related to EGFR activation. These results indicate that icariside II increased NOS activity in endothelial cells (p<0.05), but sildenafil has no significant effect on NOS activity in endothelial cells (p>0.05). The results suggest that the effect of icariside II on the regulation of NOS activity may be related to EGFR activation.

When nitric oxide synthase inhibitor LNNA was used to treat endothelial cells, the NOS baseline activity in PAE and PAE-EGFR were decreased to 2.74±0.269 u/mg and 3.27±0.319 u/mg. Treatment with nitric oxide synthase inhibitor LNNA (10-5 M) significantly inhibited the regulatory effect of icariside II on endothelial cell NOS activity in a dose dependent manner (p<0.05).

Method

1) The EGFR gene was subcloned into pGFP plasmid to construct pGFP-EGFR expression vector. With Liposome transfection reagent (Qigen), pGFP-EGFR was transfected into PAE cells. After the selection with 1800 µg/ml of G418, a single cell clone was selected. Western blot confirms the stable expression of EGFR in the PAE-EGFR cells.

2) $5\times10^5$ of the PAE cells and PAE-EGFR cells were seeded into 35 mm Petri dishes plate in quadruplicate. After 12 hours, PAE and PAE-EGFR cells was treated with 12.5 µM icariside II and sildenafil for 24 hr, respectively. Then the treated PAE and PAE-EGFR cells were lysed with RIPA buffer and subjected to 8% SDS-PAGE electrophoresis. eNOS protein expression was detect by Western blot. After development with super ECL luminescence substrate, the band was analyzed with a Optical density scanner. The results were analyzed by normalizing to β-actin.

3) $5\times10^5$ of the PAE cells and PAE-EGFR cells were seeded into 35 mm Petri dishes plate in quadruplicate. After 12 hours, PAE and PAE-EGFR cells was treated with 12.5 µM icariside II and sildenafil for 24 hr, respectively, in the presence or absence with 100 µg/ml of EGF. Then the treated PAE and PAE-EGFR cells were lysed with RIPA buffer and subjected to 8% SDS-PAGE electrophoresis. eNOS protein expression was detect by Western blot. After development with super ECL substrate, the band was analyzed with an Optical density scanner. The resulted results were analyzed by normalizing to β-actin.

TABLE 2

Effect of icariside II and sildenafil on endothelial cells (PAE) NOS enzyme activity

|  | 0 | $10^{-9}$ | $10^{-8}$ | $10^{-7}$ | $10^{-6}$ | $10^{-5}$ |
|---|---|---|---|---|---|---|
| PAE Icariside II | 6.03 ± 0.61 | 8.65 ± 0.87 | 10.71 ± 0.98 | 16.46 ± 1.63 | 19.1 ± 1.9 | 18.66 ± 1.79 |
| PAE-EGFR Icariside II | 8.35 ± 0.84 | 11.72 ± 1.21 | 15.37 ± 1.51 | 22.79 ± 2.45 | 23.91 ± 2.36 | 22.74 ± 2.27 |
| PAE Sildenafil | 6.03 ± 0.60 | 5.76 ± 0.56 | 5.85 ± 0.579 | 6.32 ± 0.63 | 5.99 ± 0.58 | 6.66 ± 0.65 |
| PAE-EGFR Sildenafil | 8.35 ± 0.79 | 8.48 ± 0.85 | 8.37 ± 0.82 | 8.53 ± 0.84 | 8.4 ± 0.84 | 8.99 ± 0.87 |

Conclusion: Icariside II significantly increases the NOS activity in endothelia cells. When EGFR is expressed, this effect is even stronger. In addition, this effect is significantly inhibited by nitric oxide synthase inhibitor. However, sildenafil showed no effect on NOS activity. These results suggest that icariside II may have preventive and therapeutic effects on endothelia cell disfunction.

Example 4

Effect of Icariside II on eNOS Expression in Vascular Endothelial Cells (PAE) and Mechanism Thereof In the previous study it was found that the expression level of EGFR and eNOS in the corpus cavernosum in diabetic patients with erectile dysfunction was significantly decreased than healthy subjects, and it was related with reduced ERK phosphorylation. These results suggest that there is crosstalk between EGF signaling pathway and NOS signaling pathway, which play a significant role in the development of erectile dysfunction.

Objectives

To study the mechanism of icariside II's regulatory effect on expression of eNOS in vascular endothelia cells.

Result

It was found that treatment with icariside II resulted in eNOS expression levels of 1.16 and 2.08 in PAE-EGFR stable strains and unstable strains, respectively. Also, the eNOS expression in PAE-EGFR stable strains was significantly increased compared to blank control and unstable strains (p<0.05). Treatment with sildenafil resulted in eNOS expression levels of 1.12 and 1.38 in PAE-EGFR stable strains and unstable strains, respectively. There was no significant difference between the stable strains and unstable strains (p>0.05).

|  | Control | Icariside II | Sildenafil |
|---|---|---|---|
| PAE | 1.01 ± 0.08 | 1.08 ± 0.09 | 1.12 ± 0.09 |
| PAE-EGFR | 1.40 ± 0.14 | 2.08 ± 0.02 | 1.38 ± 0.013 |

Conclusion:

Based on the above results, icariside II may increase the expression level of eNOS in the endothelial cells via activation of EGFR, but sildenafil did not significantly affect the expression level of eNOS. The results suggested that the effect of icariside II on eNOS expression in endothelial cells may be acted through the growth factor (EGFR) signaling pathway.

Example 5

Effect of Icariside II on NOS Activity and Intracellular Concentration of cGMP in Smooth Muscle Cell in the Corpus Cavernosum 1. Effect of Icariside II on NOS Activity in Smooth Muscle Cell in the Corpus Cavernosum Method Primary human corpus cavernosum smooth muscle cells (CCSMCs) were provided by the Andrology Center of Peking University. The CCSMCs of the third passage were cultured in six well plates for two days. Then the cells were treated with icariside II or the sildenafil at a concentration of 0, $10^{-9}$, $10^{-8}$, $10^{-7}$, $10^{-6}$, $10^{-5}$ M; or treated with icariside II (0, $10^{-9}$, $10^{-8}$, $10^{-7}$, $10^{-6}$, $10^{-5}$ M) in the presence or absence of LNNA ($4 \times 10^{-4}$ M). The control group was cultured with DMEM only. After 24 hours, the cells were washed three times and 180 μl lysis buffer was added into each well; 60 μl cell suspension was taken for protein concentration assay with BCA protein kit; 100 μl cell suspension was taken for NOS activity test. NOS activity (units/mg protein)= [(value$_{NOS\text{-}measure}$−value$_{NOS\text{-}blank}$)÷($38.3 \times 10^6$)]×[($2.15$+supernatant volume)÷($15 \times S$ supernatant volume)]÷[protein concentration in each well].

Result:

Without drug treatment, the NOS activity in the CCSMCs was 0.46 units/mg. When the concentration of icariside II is $10^{-8}$ M, NOS activity was significantly increases to 1.59 units/mg ($p<0.05$). When the concentration of icariside II is $10^{-6}$ M, the effect was peaked and NOS activity was 4.19 units/mg. There is a statistical difference when the concentration of icariside II is $10^{-7}$, $10^{-6}$ and $10^{-5}$ M ($P<0.01$). At concentrations lower than $10^{-6}$ M, icariside II's effect on NOS activity is dose dependent. On the other hand, there is no significant difference in the sildenafil group. LNNA treatment decreased the NOS activity in the CCSMCs to 0.3 units/mg protein. It was found that, in presence of NOS inhibitor LNN, icariside II is still able to increase NOS activity in a dose-dependent manner at a concentration below $10^{-6}$ M. NOS activity is not significantly increased in the LNNA group as compared with non-LNNA ($P<0.05$); the peak value of NOS activity is decreased to 2.67 unit/mg. There is significant difference at the concentration of $10^{-7}$, $10^{-6}$ and $10^{-5}$ M.

2. Effects of Icariside II on cGMP/cAMP Biosynthesis in Corpus Cavernosum Smooth Muscle Cell Method Primary human corpus cavernosum smooth muscle cells (CCSMCs) were provided by the Andrology Center of Peking University. The CCSMCs of the third passage were cultured in six plates for two days. Then the cells were treated with icariside II or the sildenafil at the concentration of 0, $10^{-9}$, $10^{-8}$, $10^{-7}$, $10^{-6}$, $10^{-5}$, M for 4 hours; or treated with icariside II or the sildenafil at the concentration of 0, $10^{-9}$, $10^{-8}$, $10^{-7}$, $10^{-6}$, $10^{-5}$, $10^{-4}$ M for 4 hours followed by a treatment with $10^{-5}$ M of SNP for 30 min. The control group was cultured with DMEM only. Then to each well was added 0.4 mL 0.1 M HCl and incubated at room temperature for 20 minutes. Then the lysed cells are harvested. The cell suspension was collected in centrifuge tubes and centrifuged at 1000 g for 10 minutes; 60 μl cell suspension was taken for protein concentration assay with the BCA protein kit, and 100 μl cell suspension was taken for cGMP or cAMP concentration test. The concentration of cGMP [pmol/(mg prot·min)]=[cGMP or cAMP concentration×supernatant volume]÷reaction time× protein concentration in each well×supernatant volume].

Result

Without drug treatment, the intracellular concentrations of cGMP and cAMP in the CCSMCs were 0.42 and 5.16 μmol/(mg prot·min), respectively. It is noted that Icariside II and sildenafil had no significant effect on the cAMP concentration ($P>0.05$).

The cGMP concentration was 2.03 μmol/(mg prot·min) and increased 4.8 times in the CCSMCs medium after treatment of $10^{-5}$ M SNP. In presence of SNP, cGMP concentration was significantly increased after treatment with icariside II or sildenafil, and $EC_{50}$ were 1.02 and 0.27 μM, respectively. Treatment with $10^{-7}$, $10^{-6}$, $10^{-5}$, $10^{-4}$ M of icariside II or sildenafil in the presence or absence of SNP makes a significant difference.

Conclusion

Icariside II and sildenafil have significantly enhanced cGMP biosynthesis in the corpus cavernosum smooth muscle cells, but the effect of icariside II on cGMP was significantly weaker than that of sildenafil. Icariside II and sildenafil did not significantly affect cAMP biosynthesis in the corpus cavernosum smooth muscle cells. This result suggested that icariside II possess some inhibitory effect on PDE5.

Example 6

Effect of Icariside II on NOS Gene Isoforms and Protein Expression in Corpus Cavernosum Smooth Muscle Cells 1. Effect of Icariside II on mRNA Expression of NOS Isoforms and PDE5a in the Corpus Cavernosum Smooth Muscle Cells Method:

Human corpus cavernosum smooth muscle cells were grown in 60 mm Petri dishes. After 12 hours, the cells were treated with icariside II or sildenafil at a final concentration of 12.5 μM for 0, 1 and 2 days. Then the treated CCSMCs were lysed with Trizol and total RNA was extracted and reverse transcribed into cDNA. PCR amplification was carried out using eNOS, iNOS, nNOS and PDE5a specific primers and the specific PCR products represent the mRNA levels.

Result

RT-PCR results showed that icariside II significantly increased nNOS mRNA levels in corpus cavernosum smooth muscle cells after 1 day and 2 days treatment ($P<0.05$, $P<0.01$) and iNOS was also slightly increased ($P<0.05$), but eNOS mRNA was not changed. PDE5a mRNA level was significantly decreased ($P<0.05$). Sildenafil significantly reduced PDE5a mRNA level after 1 day and 2 days treatment ($P<0.05$, $P<0.01$), iNOS slightly increased after 2 days treatment, but eNOS and nNOS mRNA were not significantly changed at 1 day and 2 days.

2. Effect of Icariside II on Protein Expression of NOS Isoforms and PDE5 in the Corpus Cavernosum Smooth Muscle Cells Method Corpus cavernosum smooth muscle cells were grown in 60 mm Petri dishes. After 12 hours, the cells were treated with icariside II or sildenafil at a final concentration of 12.5 μM for 0, 1 and 2 days. Then the treated CCSMCs were lysed with RIPA buffer and subjected to 8% SDS-PAGE electrophosis. Expression of eNOS and other proteins were detected by Western blot. After exposing with super ECL luminescence substrate, the band was analyzed with a Optical density scanner. The resulted results were analyzed by normalizing to β-actin.

Result

Western blot results showed that after treatment with icariside II for 1 and 2 days, the expression of nNOS, sGC and PKG protein in the corpus cavernosum smooth muscle cells was significantly increased ($P<0.05$, $P<0.01$) and iNOS was slightly increased ($P<0.05$), eNOS was also increased at 2 days ($P<0.05$). PDE5a protein were significantly decreased at 1 and 2 days ($P<0.05$, $P<0.01$). Sildenafil treatment can decrease PDE5a significantly ($P<0.01$) and increase PKG ($P<0.01$), but had no effect on eNOS, iNOS, nNOS and sGC.

Example 7

Clinical Effect of Icariside II in Patients with Erectile Dysfunction

In order to evaluate the clinical effects of icariside II on patients with sexual dysfunction, a clinical test was conducted in 28 patients suffering from sexual dysfunction (chief complaint and evaluated with international index for Erectile Function, IIEF-5) with informed consent. The clinical trial is placebo-controlled and double blinded. The mean age of the patients was $48\pm5.12$ years with a history of erectile dysfunction of $3.42\pm3.12$ years. The subjects included 12 diabetic patients and 6 traumatic ED.

Icariside II extract (containing 51% of icariside II) was prepared as capsules (each capsule contains 200 mg of icariside II). Both the administrator and the subjects are unaware of the conditions. Volunteers were randomly divided into icariside II group and the placebo group. The patients took the placebo or experimental drugs before sleep (1 capsule/time) for 4 weeks. Prior or after administration of drugs, sexual function of the patients were evaluated using the IIEF5 (5 items, each item 5 score). The sexual function change before and after administration of drugs was compared by Student t test and the efficacy was evaluated.

Results

IIEF5 scores of the subjects prior to administration of drugs were 12.6 and 13.2 for the treatment and placebo groups, respectively. After administration of drugs, the IIEF5 score were $19.54\pm3.67$ and $14.23\pm2.97$ for the treatment and placebo groups, respectively. It is shown that the erective function in icariside II group was significantly improved compared to placebo group ($p<0.05$). The overall clinical effect was 71.41% and 41.48% for icariside II and placebo groups, respectively. There were no significant side effects except that 3 patients showed a mild gastric intestinal tract reaction. There was no significant difference in clinical efficacy and side effects among patients with diabetic, hypertension and cardiac diseases.

Conclusion: This clinical result suggested that extracts comprising icariside II has an effect in improving the erectile dysfunction for the patients with pathological or organic tissues, and could be effectively and safely applied for patients with erectile dysfunction.

What is claimed is:

1. A method for treating male or female sexual dysfunction comprising administering to a patient in need thereof a composition comprising icariside II in an amount and for a duration effective to improve sexual function in a male or female.

2. The method according to claim 1, wherein the effective amount is 5-500 mg per day.

3. The method according to claim 1, wherein the composition is administered to said patient for at least four weeks.

4. The method according to claim 1, wherein the composition is administered orally.

5. The method according to claim 1, wherein the effective amount is 200 mg per day.

6. The method according to claim 1, wherein the icariside II is administered as an extract comprising icariside II.

7. The method according to claim 1, wherein the composition further comprises a pharmaceutically acceptable carrier or excipient.

8. The method of claim 1, in which the sexual dysfunction is erectile dysfunction.

9. The method of claim 1, in which the patient is diabetic.

10. The method of claim 1, wherein the icariside II is administered in an amount and for a duration effective to increase NOS activity in vascular endothelial cells in the patient.

11. The method of claim 1, wherein the icariside II is administered in an amount and for a duration effective to promote nerve regeneration in the patient.

* * * * *

UNITED STATES PATENT AND TRADEMARK OFFICE
CERTIFICATE OF CORRECTION

PATENT NO.       : 8,530,433 B2
APPLICATION NO.  : 12/997423
DATED            : September 10, 2013
INVENTOR(S)      : Xin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 206 days.

Signed and Sealed this
Fifteenth Day of September, 2015

Michelle K. Lee
*Director of the United States Patent and Trademark Office*